US009895293B2

(12) United States Patent
Blank

(10) Patent No.: US 9,895,293 B2
(45) Date of Patent: Feb. 20, 2018

(54) ILLUMINATED NIPPLE SHIELD

(71) Applicant: Amber Michelle Blank, Cincinnati, OH (US)

(72) Inventor: Amber Michelle Blank, Cincinnati, OH (US)

(*) Notice: Subject to any disclaimer, the term of this patent is extended or adjusted under 35 U.S.C. 154(b) by 0 days.

(21) Appl. No.: 15/013,187

(22) Filed: Feb. 2, 2016

(65) Prior Publication Data

US 2016/0220451 A1 Aug. 4, 2016

Related U.S. Application Data

(60) Provisional application No. 62/111,082, filed on Feb. 2, 2015, provisional application No. 62/112,097, filed on Feb. 4, 2015.

(51) Int. Cl.
*A61J 13/00* (2006.01)
*A61B 90/30* (2016.01)

(52) U.S. Cl.
CPC ......... *A61J 13/00* (2013.01); *A61B 2090/304* (2016.02); *A61J 2205/20* (2013.01)

(58) Field of Classification Search
CPC ........ A61J 17/001; A61J 17/005; A61J 13/00; A61J 2205/20; A61B 2090/304
USPC ................ 606/234, 236, 235, 239; 600/249; 362/154, 801; 128/359, 360; 215/11.1, 215/11.5
See application file for complete search history.

(56) References Cited

U.S. PATENT DOCUMENTS 2,364,866 A 12/1944 Meynier
4,688,571 A * 8/1987 Tesler .................. A61J 17/005 606/234
4,832,214 A 5/1989 Schrader et al.
5,522,848 A * 6/1996 Kamali ................ A61J 17/005 606/234
D381,752 S 7/1997 McCoy
D417,735 S 12/1999 Ford
7,074,345 B2 7/2006 Saito et al.
(Continued)

FOREIGN PATENT DOCUMENTS

KR 20010007462 U 7/2011

OTHER PUBLICATIONS

International Search Report and Written Opinion of the International Searching Authority, dated May 13, 2016, for corresponding International Application No. PCT/US2016/016103, filed Feb. 2, 2016 (13 pages).

*Primary Examiner* — Pedro Philogene

(74) *Attorney, Agent, or Firm* — Hasse & Nesbitt LLC; Daniel F. Nesbitt

(57) ABSTRACT

A nipple shield containing a luminescent agent that illuminates for visibility in darkened conditions. The nipple shield has a nipple portion and a base portion that extends from the nipple portion formed of a resin material such as silicone that contains the luminescent agent, such as a photoluminescent pigment. The base portion or an outer annular part can contain the luminescent agent. The nipple shield or only the base portion can be a formed film that has a resin material layer that contains substantially no luminescent agent, and a layer that contains the molded resin material and the luminescent agent. An illuminating nipple shield can also be a nipple shield rim containing the luminescent agent that conforms and adheres releasable to the base portion of a conventional nipple shield.

9 Claims, 4 Drawing Sheets

(56) References Cited

U.S. PATENT DOCUMENTS

| | | | | |
|---|---|---|---|---|
| D637,726 | S | 5/2011 | Francis | |
| 8,852,479 | B2 | 10/2014 | Sutter | |
| 2006/0157065 | A1 * | 7/2006 | Rohrig .................... | A61J 13/00 128/890 |
| 2007/0031685 | A1 | 2/2007 | Ko et al. | |
| 2009/0283101 | A1 | 11/2009 | Mans | |
| 2011/0065360 | A1 | 3/2011 | Francis | |
| 2014/0008317 | A1 | 1/2014 | Yang et al. | |

* cited by examiner

ILLUMINATED NIPPLE SHIELD

CROSS REFERENCE TO RELATED APPLICATION

The present invention claims the benefit of U.S. Provisional Application 62/111,082, filed Feb. 2, 2015, and U.S. Provisional Application 62/112,097, filed Feb. 4, 2015, the disclosures of which are incorporated by reference.

FIELD OF INVENTION

The invention relates to infant breast feeding.

BACKGROUND OF THE INVENTION

The primary function of a nipple shield (also referred to as nipple guard or protector) is to aid in breastfeeding an infant. Currently manufactured from transparent silicone material, the nipple shield fits directly over a mother's nipple typically in a cylindrical shape with a base conforming to the breast. Holes are present to the tip of the nipple shield allowing transfer of mother's breast milk via the nipple shield to the nursing infant.

There are many indications for usage including, but not limited to, latch complications related to the infant; flat, inverted or tight nipples from the mother; disorganized or premature sucking related to the infant; etc. Additionally, the nipple shield also prevents and/or allows for healing in mothers with sensitive, sore, irritated, damaged or injured nipples related to breastfeeding. The nipple shield has existed for many years with modifications including changes in material (previous materials included rubber or latex), product thickness (related to material), shape and design/variations of base, shape and design of nipple, and modifications to the nipple openings through which breast milk flows. All modifications have maintained the nipple shield to be manufactured with a transparent material.

Current manufacturing of the nipple shield is done with the use of a transparent BPA-free silicone material. While the transparent silicone material allows for visibility of the mother's nipple, it is very difficult to use for breastfeeding during nighttime and/or darkened conditions. Breastfed infants generally nurse every 2-3 hours throughout a 24 hour period, including nighttime. The transparent material of current nipple shields may contribute to many related complications at night including loss of the nipple shield, improper placement of the nipple shield upon the breast, and complications related to improper placement. If a nipple shield is placed incorrectly (not centered on the mother's nipple) it could lead to damage, sensitivity, irritation and/or soreness to the nipples. Additionally, this complication might also result in inefficient transfer of milk.

SUMMARY OF THE INVENTION

The present invention provides an improvement to breast feeding that reduces complications associated with nighttime and/or use in darkened conditions. The present invention provides an improved nipple shield that improves the effectiveness and experience of breastfeeding during nighttime and/or darkened conditions, for the breastfeeding mother, the infant and a caregiver.

The invention provides an improved nipple shield that illuminates for visibility in darkened conditions, including at nighttime, to provide ease of use and visibility for nighttime and darkened-condition breastfeeding.

An aspect of the invention is an illuminated nipple shield that illuminates for visibility in darkened conditions, which includes a nipple portion and a base portion extending from the nipple portion. The illuminated nipple shield includes a molded resin material that contains a luminescent agent. The resin material itself can be transparent, translucent or opaque to light.

The illuminated nipple shield and its manufacture utilizes luminescent technology to illuminate the nipple shield or a portion thereof, including the base portion, to provide an illuminated, glow-in-the-dark product. Luminescent technology may include, but is not limited to, luminescent agents selected from the groups consisting of phosphorescence, photoluminescence, fluorescence, chemiluminescence, bioluminescence, radioluminescence, incandescence, and electroluminescence. The luminescence can be emitted in a variety of colors. The luminescent agent is a material that can include, but not be limited to, luminescent powder, liquid, gel or pigments.

The present invention also provides an illuminated element made into a form for association with or attachment to, a conventional nipple shield, to form an illuminated nipple shield. The illuminated element can be any shape, including, but not limited to, ring, arc, circular dots, ovals, rectangles, and elongated stripes. The illuminated element can be attached permanently or removably to the nipple shield. The form of the illuminated element can include, but not be limited to, a band, a tape, a rim, a label and a tag. The illuminated element can be made of a carrier material onto or into which is applied the illuminated material and/or the luminescent agent. The carrier material can include paper, paperboard, and a thermoplastic, resinous, elastomeric, or polymeric sheet. The carrier material can include the same material from which the nipple shield is made. The rim, band, tape or tag can be applied or associated with the nipple shield using an adhesive, such as a pressure sensitive adhesive, an epoxy, or other conventional adhesives, or can be attachable by surface to surface adhesion with the nipple shield. A release layer of material can be temporarily attached to the adhesive material to prevent premature attachment and contamination of the adhesive material. The release layer is typically a thermoplastic film. The illuminated material can be applied or used in combination with other materials, including a reflective material.

Another aspect of the invention is an illuminated nipple shield that includes an illuminated rim, either affixed or attachable, permanently or removably, to a nipple shield, to provide ease of use and visibility for nighttime and darkened-condition breastfeeding. The illuminated rim can have an annular shape that fits along the entire circumference of the nipple shield, or an arcuate shape that fits selectively along a portion of the circumferential periphery of the nipple shield.

Another aspect of the invention is a kit or a combination of a conventional nipple shield and an attachable illuminated element.

The present invention also provides a method for illuminating a conventional nipple shield for visibility in a darkened environment, by applying to a portion of a conventional nipple shield, permanently or removably, an illuminated element as described herein.

The invention provides an illuminated nipple shield or an illuminated element with a full range of luminescent glow, as determined by rating or brightness, grade (chemical purity and bonding effectiveness), coated/non coated, dim rate or length, particle size, and/or any other measure of the luminescent product as deemed in the industry to achieve the optimal performance.

The inclusion of a luminescent agent or an illuminated material in the nipple shield, and more particularly in the base of the nipple shield, or in an illuminated element attachable to the base of the nipple shield, can provide or include a design or appearance in the form of any character(s), picture(s), symbol(s), letter(s), number(s), or any other appropriate form, and combinations thereof.

The illuminated nipple shield, or an illuminated element that attaches to a conventional nipple shield currently in the market, can be manufactured by combining the luminescent technology to the current manufacture materials, which can include, but is not limited to, silicone, BPA-free plastics, latex and rubber, and can include modifications to the shape and mode of manufacture of the base, the nipple, and the nipple openings.

DETAILED DESCRIPTION OF THE INVENTION

Definitions

As used herein, the phrase "a conventional nipple shield" means any device commonly referred to as a nipple shield that is placed over a nipple and a portion of the breast surrounding the nipple of a breast-feeding mother for nursing an infant, including a nipple portion with at least one opening in the tip and disposed over the nipple and a base portion at least partially surrounding the nipple portion. Conventional nipple shield includes any and all previously made and marketed nipple shield and any disclosed by publication, regardless of shape, size and features or modifications to the nipple portion of the base portion.

Figure 1:
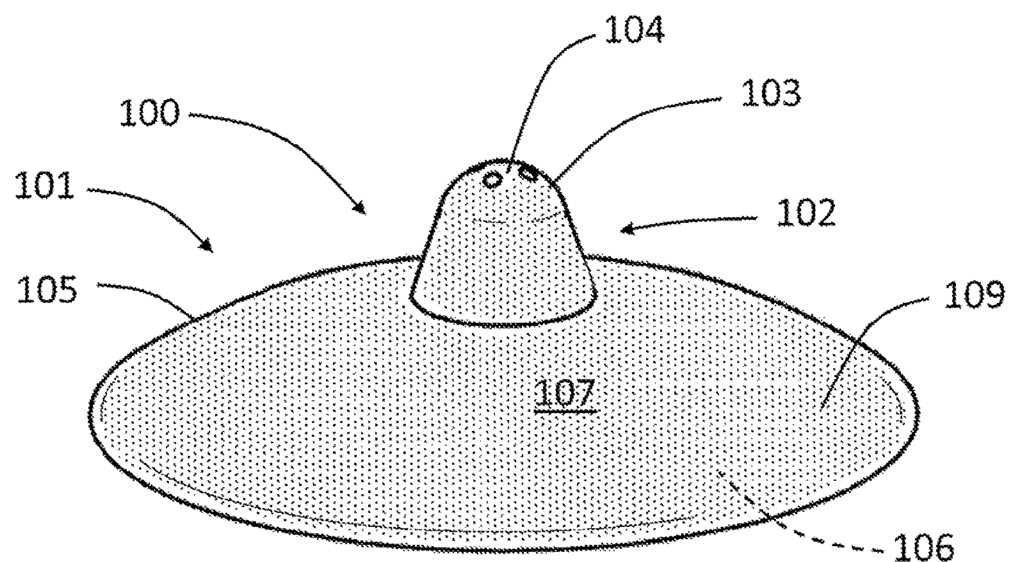
FIG. 1 shows an illuminated nipple shield including a nipple portion and a base portion, made of a material containing a photoluminescent pigment.

FIG. 1 shows an illuminated nipple shield 100 of the present invention. The nipple shield 100 includes a base portion 101 extending annularly from a base end of a nipple portion 102 to an outer peripheral edge 105. The base portion 101 includes a sheet having a domed, annular shape, and having an inner-facing concave surface 106 that conforms to the breast of a breastfeeding mother, and an outer-facing surface 107. The nipple portion 102 accepts the mother's nipple, the nipple portion 102 having openings 104 at the tip 103 that allow transfer of the breast milk from the mother to a nursing infant. The illuminated nipple shield is made of an illuminated material 109 containing a luminescent agent. A non-limiting example of a luminescent agent is a photoluminescent agent.

Figure 2:
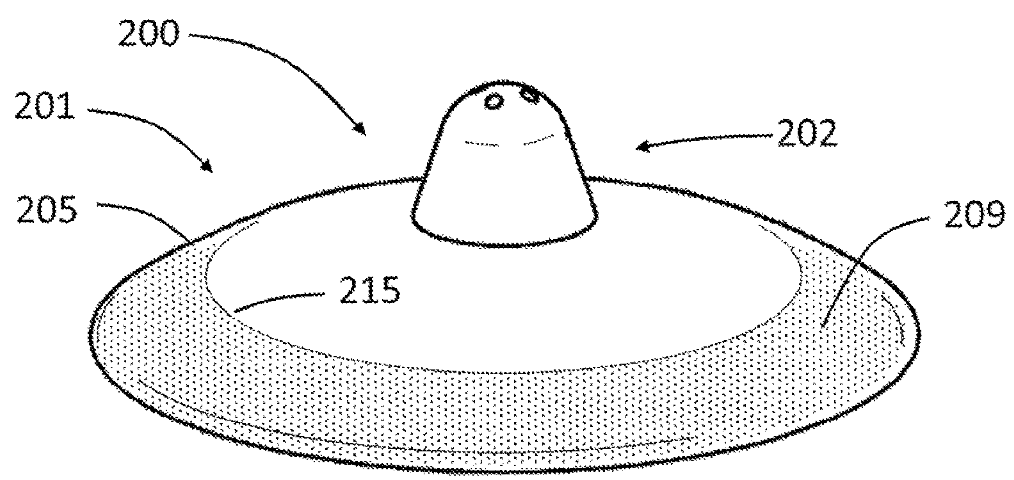
FIG. 2 shows an illuminated nipple shield having a portion of the base portion containing the photoluminescent pigment.

In an alternative embodiment shown in FIG. 2, an illuminated nipple shield 200 includes a base portion 201 and a nipple portion 202, where the illuminated material 209 is comprised in only an annular segment of the base portion 201 extending from the outer peripheral edge 205 inwardly to an inner boundary 215.

Figure 3:
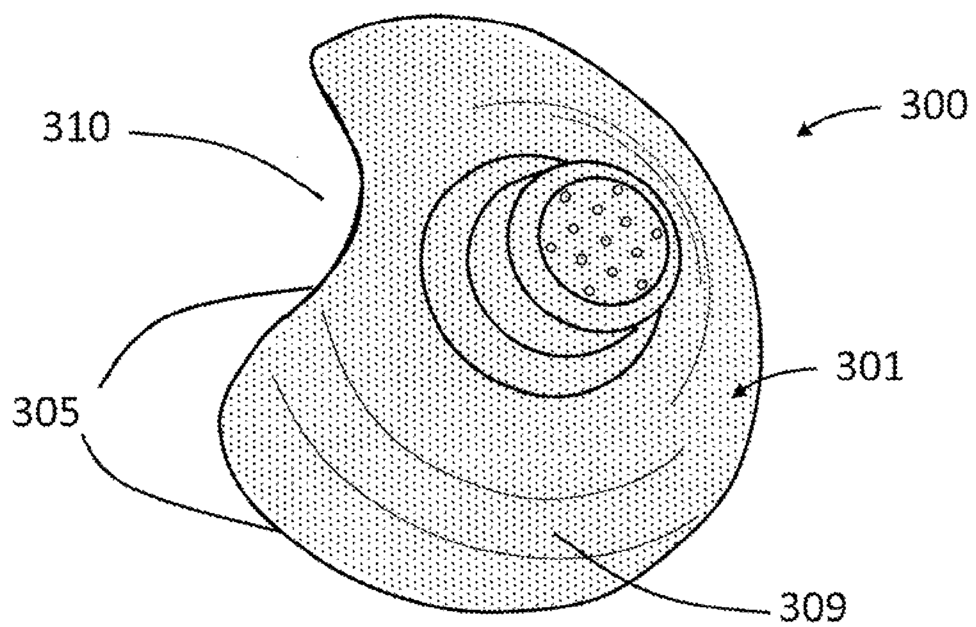
FIG. 3 shows another embodiment of a conventionally-shaped nipple shield having a cut-out portion in the rim, and made of a material containing a photoluminescent pigment.

Alternative embodiments of the invention can include modifications to the design, shape and size of the base portion and the nipple portion of a nipple shield as are known in the nipple shield art and market. FIG. 3 shows a non-limiting example of another conventionally-shaped illuminated nipple shield 300 made of an illuminated material 309 containing a luminescent agent, having a base portion 301 with a peripheral edge 305, and having a concave-shaped indentation 310 extending in from the edge 305 of the base portion 301. Non-limiting examples of conventionally-shaped nipple shields can be found in US Patents/Patent Publications U.S. Pat. No. 2,364,866, D637,726, D381,752, US 2007/0283101, and US 2011/0065360, the disclosures of which are incorporated by reference in their entireties.

In other aspects of the invention, the material of the illuminated nipple shield comprises a transparent molded resin material that contains a luminescent agent. The entire nipple shield can be made of the illuminated molded resin material. In an alternative embodiment, only a portion of the nipple shield contains the luminescent agent. In an example, the base portion only contains the luminescent agent. In another example, only a part of the sheet of the base portion, such as an outer annular part of the sheet, contains the luminescent agent.

Non-limiting examples of resin materials processed to contain one or more luminescent agents can be found in US Patents/Patent Publications U.S. Pat. Nos. 8,852,479, 7,074,345, and US 20070031685, the disclosures of which are incorporated by reference in their entireties. Such non-limiting examples include methyl methacrylate resins, unsaturated polyester resins, epoxy resins, and silicone resins. In some embodiments, the resin material is transparent. In further embodiments, the transparent resin material is a silicone resin.

In a preferred embodiment, the luminescent agent is a photoluminescent pigment having a relatively small mean particle size dispersed within a resin material, and formed into the shape of the nipple shield or attachable illuminated element or rim. The photoluminescent pigments are protected exceptionally well by the cured silicone material against any liquid media from the outside, including expressed breast milk and the infant's saliva. Those skilled in the art would appreciate that many photoluminescent pigments are insoluble in water and the molten resin material and thus form a suspension within the resin material after it has been cured and formed into the shape of a nipple shield. As disclosed in U.S. Pat. No. 7,074,345, the amount of resin material used may be in the range of 7 to 95 wt % based on the total weight of the photoluminescent pigment, although in the case where the resin material is present in concentrations less than 7 wt %, its function as a matrix that disperses, binds, and holds the photoluminescent pigment is decreased or lost. The photoluminescent pigment typically has a mean particle size of less than about 2000 μm.

Preferably, the mean particle size is less than about 150 μm, and particularly preferably less than about 120 μm, and more particularly preferably less than about 100 μm. A separate encapsulation or other treatment of the silicone matrix to isolate or protect the photoluminescent pigments is not required and is not used.

The amount of the luminescent agent contained within the molded resin material can be sufficient to be visible in a dark or darkened environment for at least 2 hours, including at least 4 hours, at least 6 hours, at least 8 hours, and at least 12 hours, after exposure to an amount of light sufficient to activate luminescently the luminescent agent. It can be understood that the luminesce or light being emitted from the luminescent agent, when fully or partially activated, contained in the material of the illuminated nipple shield or a portion thereof, is a visible light that can be viewed under darkened conditions, but may not be visible with the unaided eye in daylight, lighted or bright conditions.

The emitted color of the photoluminescent pigment, and therefore of the nipple shield or attachable rim, can be selected from those available in the industry. If the nipple shield is intended to glow in a different color from that predetermined by the photoluminescent pigment, the silicone carrier material can be separately colored to achieve the desired glow color.

A non-limiting example of a photoluminescent agent comprises strontium aluminate, which provides sufficient brightness and has sufficiently long persistence. Several commercial pigments containing strontium aluminate, including multiple versions of the Ultra Green V10 photoluminescent pigment, possess a mean particle size of less than 100 microns.

Figure 4:
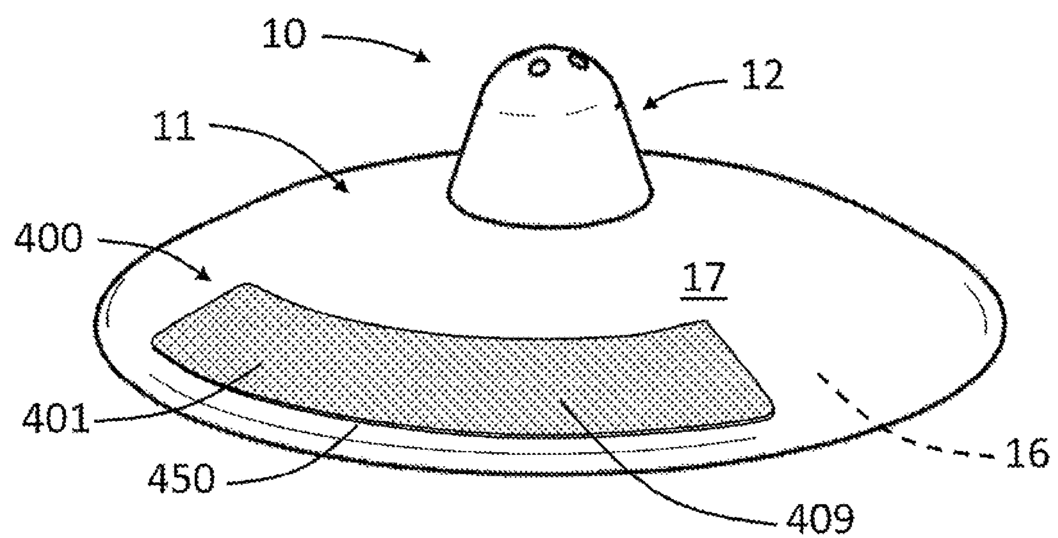
FIG. 4 shows an embodiment of a conventionally-shaped nipple shield having an illuminated strip attached to its base portion.
Figure 5:
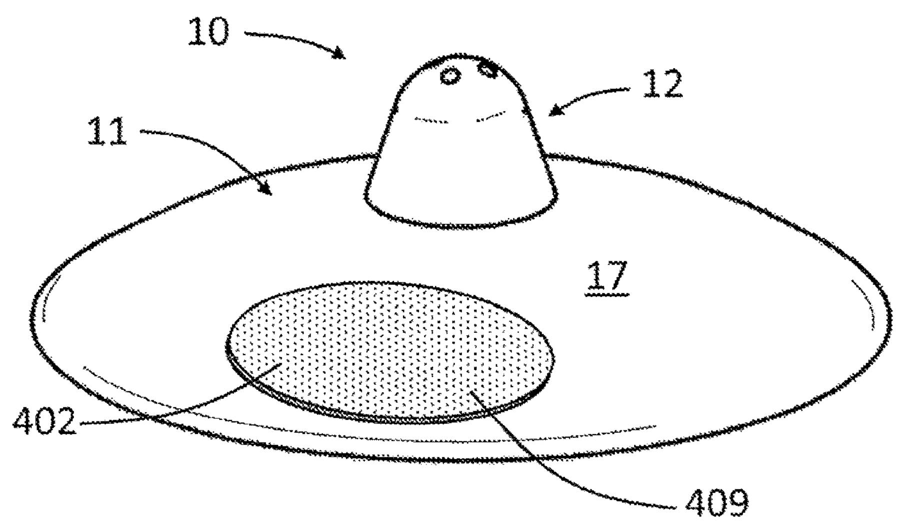
FIG. 5 shows the conventionally-shaped nipple shield having an illuminated tag attached to its base portion.

FIG. 4 shows another embodiment of the invention of an attachable illuminated element 400 attached to the outer-facing surface 17 of the base portion of a conventional nipple shield 10. Optionally, the attachable illuminated element 400 can be attached to the skin-facing surface 16 of the nipple shield 10. The illustrated illuminated element 400 is an arcuate strip 401 containing the illuminated material 409, and includes an adhesive material 450 on an under surface for adhesively attaching the strip 401 to the base portion 11 of the conventional nipple shield 10. The attachable illuminated element 400 can be any other shape and size. FIG. 5 shows, by example, an oval-shaped illuminated tag or label 402 containing the illuminated material 409. The illuminated material can include a silicone resin material containing a photoluminescent agent. The silicone resin material can be the same material from which the conventional nipple shield is made.

Figure 6:
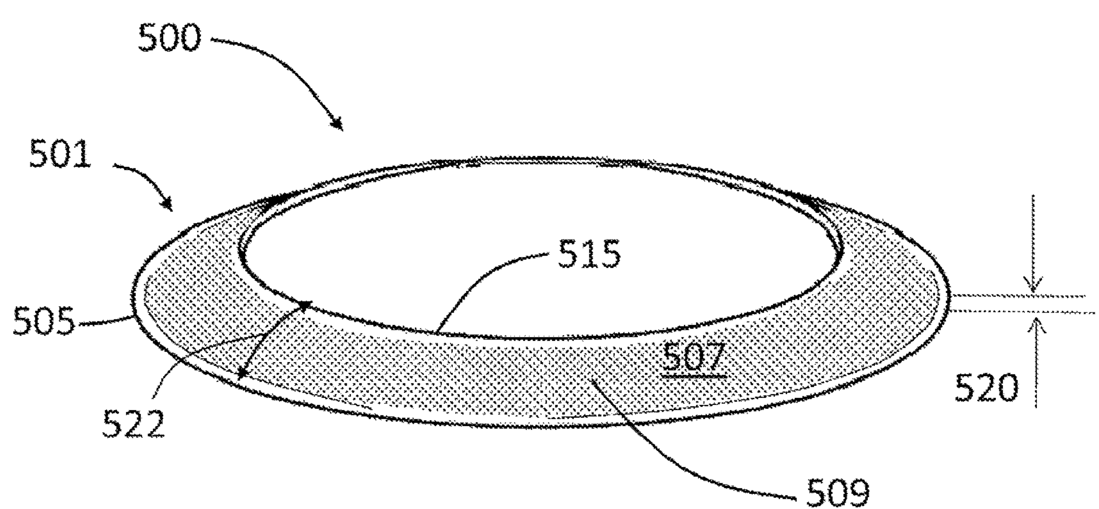
FIG. 6 shows a separate illuminated rim made of a material containing a photoluminescent pigment.
Figure 7:
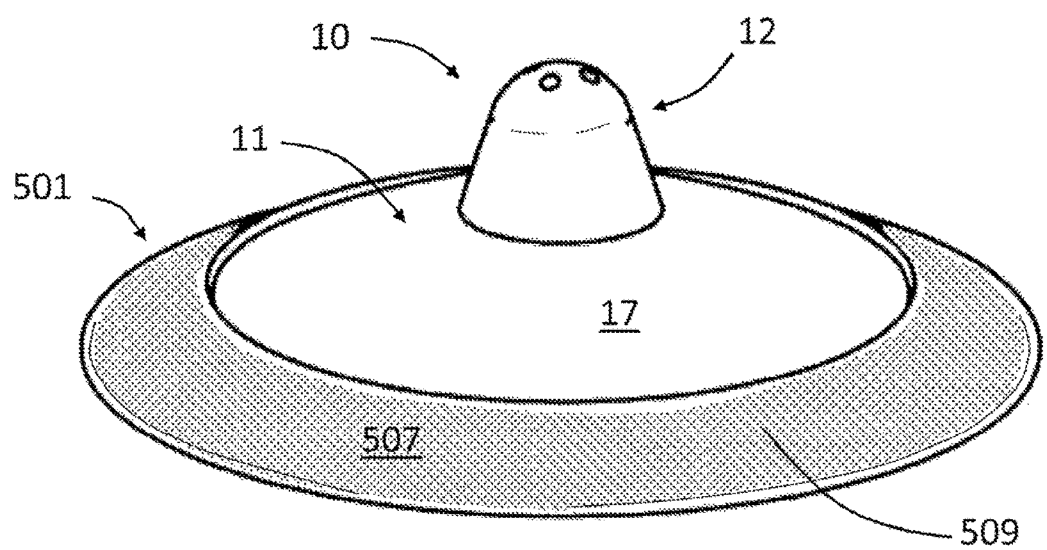
FIG. 7 shows the separate illuminated rim of FIG. 6, attached to a base portion of a conventional nipple shield.

FIG. 6 shows another embodiment of the invention of an attachable illuminated element 500 consisting of an illuminated nipple shield rim 501 that can be removably affixed to a conventional nipple shield. The rim 501 has an annular shape having an outer surface 507, defined by an inner edge 515 and outer edge 505, and dimensions and shape for conforming to and attaching along the peripheral edge of the outer-facing surface 17 of the base portion 11 of the conventional nipple shield 10, as shown in FIG. 7. The inner edge 515 defines an opening that is configured in shape and size to accept the nipple portion 12 of the conventional nipple shield. The thickness 520 and the radial depth 522 of the nipple shield rim 501 placed on the base portion 11, can have any effective and sufficient dimension for manufacturability and functionality.

The illuminated material 509 of the nipple shield rim 501 can comprise the molded resin material containing a luminescent agent. The resin material itself can be transparent, translucent or opaque to light. The molded resin material is configured to conform and adhere, sufficiently and releasably, to the molded resin material of the base portion 11 of the conventional nipple shield 10.

Figure 8:
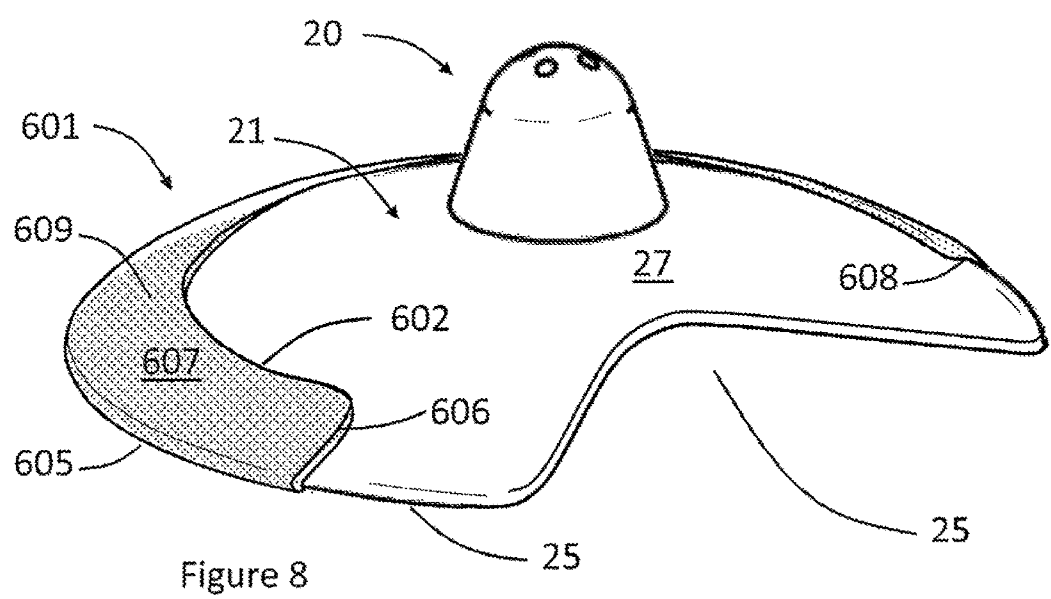
FIG. 8 shows another embodiment of a separate illuminated rim, having an arcuate shape and attached to a portion of the edge of a base portion of the conventional nipple shield of FIG. 3.

FIG. 8 shows an alternative embodiment of an illuminated nipple shield rim 601 having an arcuate shape having an outer surface 607, defined by an inner edge 602 and outer edge 605, and opposed ends 606 and 608. The shield rim 601 has a dimension and shape for conforming to the base portion 21 of the conventional nipple shield 20, illustrated as having a shape and design similar to, but limited by, that of the nipple shield shown in FIG. 3. The arcuate-shaped rim 601 extends over an arcuate portion of the top surface 27 of the nipple shield, and extends to the ends 606 and 608 to attach along only a portion of the peripheral edge 25 of the nipple shield 20, and can be attached to leave uncovered the indentation 28 in the base portion 21 of the nipple shield 20. The illuminated material 609 of the nipple shield rim 601 can comprise the molded resin material containing a luminescent agent.

In an embodiment of the invention, the nipple shield that includes the nipple portion and the base portion can be made as a single unitary formed sheet or film. The formed sheet or film can include a single material layer that comprises the molded resin material containing the luminescent agent. In an alternative embodiment, the formed sheet or film can include two or more distinct layers, including at least one resin material layer that contains substantially no luminescent agent, and at least one layer that comprises the molded resin material containing the luminescent agent. The breast-contacting surface of the nipple shield can consist of the resin material layer that contains substantially no luminescent agent, or can consist of the layer that comprises the molded resin material containing the luminescent agent. The infant-facing surface of the nipple shield can consist of the resin material layer that contains substantially no luminescent agent, or can consist of the layer that comprises the molded resin material containing the luminescent agent. In another embodiment, the formed sheet or film can include a middle layer that contains the molded resin material containing the luminescent agent, and a layer of the resin material that contains substantially no luminescent agent on the opposite sides of the middle layer, such that a material that contains the luminescent agent is not directly in contact with their the breast or the infant.

In such embodiments or in another embodiment of the invention, only a portion of the single unitary formed sheet or film contains the luminescent agent. The luminescent agent-containing portion can include the base portion or the nipple portion. The luminescent agent-containing portion can include a portion only of the base portion, or of the nipple portion.

In another embodiment of the invention, the nipple shield rim can be made as a single unitary formed sheet or film. The formed sheet or film can include a single material layer that comprises the molded resin material containing the luminescent agent. In an alternative embodiment, the formed sheet or film can include two or more distinct layers, including at least one resin material layer that contains substantially no luminescent agent, and at least one layer that comprises the molded resin material containing the luminescent agent. The infant-facing surface of the nipple shield rim can consist of the resin material layer that contains substantially no luminescent agent, while the nipple shield-contacting and connecting surface of the nipple shield rim can consist of the resin material layer containing the luminescent agent.

The nipple shield and its components, and the nipple shield rim, can be made by any or a combination of conventional processes, including injection molding, extrusion molding, blow molding, coating, dipping spraying, deposition, master-batch manufacturing, and other processes known for the making of nipple shield devices and similar articles.

I claim:

1. An illuminated nipple shield that can illuminate for placement of the nipple shield on a breast in darkened conditions, the nipple shield is formed of a transparent or translucent resin material comprising about 7% to about 95% by weight of the nipple shield, the nipple shield including a nipple portion and a base portion extending from the nipple portion, the nipple shield including a luminescent agent having a mean particle size of less than about 2000 μm that is interspersed within a portion of the transparent resin material.

2. The nipple shield according to claim 1 wherein the resin material is a transparent resin material.

3. The nipple shield according to claim 2 wherein the transparent resin material is a silicone.

4. The nipple shield according to claim 3 wherein the luminescent agent is a photoluminescent pigment.

5. The nipple shield according to claim 2 wherein the luminescent agent is a photoluminescent pigment.

6. The nipple shield according to claim 1 wherein the base portion comprises a sheet extending annularly from a base end of the nipple portion, and the luminescent agent is contained only in the base portion.

7. An illuminated nipple shield that can illuminate for visibility in darkened conditions, including a nipple portion and a base portion extending from the nipple portion, the nipple shield being formed of a resin material, the nipple shield including a photoluminescent pigment agent, wherein the photoluminescent pigment agent is contained in an outer annular portion of the base portion.

8. The nipple shield according to claim 6, wherein the photoluminescent pigment agent is contained only in an outer annular portion of the base portion.

9. The nipple shield according to claim 7, wherein the nipple portion and the base portion comprise a formed film that includes two or more distinct layers, including a resin layer that contains substantially no photoluminescent pigments, and a layer that comprises the molded resin material and the photoluminescent pigments.

* * * * *